(12) United States Patent
Yoon

(10) Patent No.: US 8,211,413 B2
(45) Date of Patent: Jul. 3, 2012

(54) METHOD AND COMPOSITION FOR PREVENTING COLORING OF THE SKIN ADJACENT THE HAIRLINE WHEN DYING A PERSON'S HAIR

(75) Inventor: Sang H. Yoon, Winter Park, FL (US)

(73) Assignee: You See, LLC, Apopka, FL (US)

( * ) Notice: Subject to any disclaimer, the term of this patent is extended or adjusted under 35 U.S.C. 154(b) by 320 days.

(21) Appl. No.: 12/655,838

(22) Filed: Jan. 11, 2010

(65) Prior Publication Data

US 2011/0167571 A1     Jul. 14, 2011

(51) Int. Cl.
*A61K 8/00*     (2006.01)
(52) U.S. Cl. .................................. 424/70.1; 424/78.02
(58) Field of Classification Search .................. 424/70.1
See application file for complete search history.

(56) References Cited

U.S. PATENT DOCUMENTS

| 5,437,860 | A | 8/1995 | Jarvis et al. |
| 5,500,218 | A | 3/1996 | Kischka et al. |
| 5,607,979 | A | 3/1997 | McCreery |
| 6,649,175 | B1 | 11/2003 | Haslwanter et al. |

*Primary Examiner* — Jake M. Vu
(74) *Attorney, Agent, or Firm* — William M. Hobby, III

(57) ABSTRACT

The present invention relates to a method of dying a person's hair and especially to a method and composition for preventing coloring of the skin adjacent the hairline when dying a person's hair. The composition for applying to a person's skin adjacent the hairline to prevent coloring of the skin adjacent the hairline when dyeing a person's hair includes a mixture of alcohol, polyvinylpyrrolidone, polyvinyl alcohol, glycerin, ethylhexyl palminate, bambusa starch octenylsuccinate, zinc oxide, titanium dioxide, polyethylene glycol, dimethicone, allantoin and water.

12 Claims, No Drawings

METHOD AND COMPOSITION FOR PREVENTING COLORING OF THE SKIN ADJACENT THE HAIRLINE WHEN DYING A PERSON'S HAIR

BACKGROUND OF THE INVENTION

The present invention relates to a method of dying a person's hair and especially to a method and composition for preventing coloring of the skin adjacent the hairline when dyeing a person's hair.

When dyeing a person's hair, even when the hair dye composition is applied with the utmost care, coloring of the skin cannot always be avoided. This coloring of the skin is particularly unsightly when visible on the skin along the hairline.

Numerous color spot removers have been used after the hair dyeing treatment for removing color spots from the skin. The removal of color spots in this manner is always irritating to the skin due to the cleaning materials in the spot cleaning solutions and because of the mechanical rubbing of the skin to remove the spots.

To prevent the coloring of the skin when dyeing the hair, skin creams in the form of oil in water emulsions or water in oil emulsions and petrolatum are sometimes applied directly to the hairline before the hair dyeing treatment. The use of skin protection compositions in the form of emulsions, particular in hair dyeing treatments with dark, color intensive shades does not adequately protect the skin from coloring and subsequent treatment with color spot remover is required.

The present invention overcomes these disadvantages by using a method having a composition that forms a mask over the skin adjacent the hairline which can be peeled off to remove any dye which may have gotten thereon and which is peeled off without hurting the person being treated.

In the prior U.S. Pat. No. 5,500,218 to Kischka et al, a method of preventing coloring of the skin adjacent the hairline during dyeing of hair is provided which composition contains polyethylene glycol, hydrogenated castor oil, ethoxylated with ethylene oxide, glycerin and polyethylene glycol and a cosmetic additive and water. This coating is applied to the skin during dyeing of the hair and then rinsing the hair.

The Haslwanter et al. U.S. Pat. No. 6,649,175 is for a skin barrier composition for protection against contact with irritants. The composition has long-chain fatty acid, long-chain fatty alcohol, hydrocarbon oil, silicone skin protectant, alkanolamine, Humectant, inorganic skin protectant, a preservative and water.

The Jarvis et al. U.S. Pat. No. 5,437,860, is for a skin and scalp barrier composition for the protection of skin and scalp during hair relaxer treatment for use with hair treatment products. The Kalopissis et al. U.S. patent is a hair dying process involving protection of the scalp. The process applies a composition based on a substance of vegetable or animal origin, a synthetic organic substance or mineral substance to limit the passage of dyestuffs when dying the hair. In U.S. Pat. No. 6,387,382, to Saleh et al. is for a multipurpose skin preparations in the form of oil-in-water emulsions for forming a water-proof, respirable, skin barrier composition. The McCreery U.S. Pat. No. 5,607,979 is for a topical skin protectant.

The present process is for a method of preventing coloring of the skin adjacent the hairline when dyeing a person's hair and to the composition used in the process.

SUMMARY OF THE INVENTION

The present invention relates to a method of dyeing a person's hair and especially to a method and composition for preventing coloring of the skin adjacent the hairline when dyeing a person's hair.

The composition for applying to a person's skin adjacent the hairline to prevent coloring of the skin adjacent the hairline when dyeing a person's hair includes: 2-20% by weight of alcohol, 1-8% by weight of polyvinylpyrrolidone, 1-10% by weight of polyvinyl alcohol, about 1% by weight of glycerin, 1-15% by weight of ethylhexyl palmitate, 0.5-5% by weight of bambusa vulgaris extract, 0.2-5% by weight of steareth, 0.5-5% by weight of aluminum starch octenylsuccinate, 0.5-5% by weight of zinc oxide, 0.5-5% by weight of titanium dioxide, 1.-10% by weight of polyethylene glycol, 0.5-10% by weight of dimethicone, 0.05-1% by weight of allantoin and 30-70% by weight of water.

The process of preventing coloring of the skin adjacent the hairline when dyeing a person's hair includes preparing the composition lotion for applying to a person's skin adjacent the hairline and then applying the composition in lotion form along the hairline of a person before dyeing their hair to form a peel-able mask over the skin adjacent the hairline. The person's hair is then dyed and then the mask is peeled from the person's skin after the hair has been dyed to remove the mask coating and any dye that may have gotten thereon.

DETAILED DESCRIPTION OF THE INVENTION

The present invention relates to a method of dyeing a person's hair and especially to a method and composition for preventing coloring of the skin adjacent the hairline when dyeing a person's hair.

The composition for applying to a person's skin adjacent the hairline to prevent coloring of the skin adjacent the hairline when dyeing a person's hair include a mixture as follows, all percentages (%) being by weight unless otherwise indicated: about 2-20% by weight of alcohol, such as SD40A alcohol (ethyl alcohol); about 1-8% by weight of polyvinylpyrrolidone (PVP), a water soluble polymer made from the monomer N-vinylpyrrolidone: about 0.1-10% by weight of polyvinyl alcohol (PVOH), a water soluble synthetic polymer; about 1% by weight of glycerin (also commonly called glycerol or glycerine), which may include glyceryl acrylate/acrylic acid copolymer; about 1-15% by weight of ethylhexyl palmitate (or octyl palmitate), an ester of 2-ethylhexanol and palmitic acid commonly used in cosmetic formulations; about 0.5-5% by weight of bambusa vulgaris extract, a bamboo extract; about 0.2-5% by weight of steareth, such as Steareth-10, a polyethylene glycol ether of stearci acid; about 0.5-5% by weight of aluminum starch octenylsuccinate, an aluminum salt of the reaction product of octenylsuccine anhydride with starch; about 0.5-5% by weight of zinc oxide, .about 5-5% by weight of titanium dioxide, about 1.-10% by weight of polyethylene glycol, such as PEG 400 Polyethylene Glycol, which is a low molecular weight grade of Polyethylene glycol; about 0.5-10% by weight of dimethicone (Polydimethylsiloxane), which belongs to the group of polymeric organosilicon compounds commonly referred to as silicones; about 0.05-1% by weight of allantoin, also called 5-ureidohydantoin or glyoxyldiureide; and 30-70% by weight of water. The composition may also have about 0.2-1.5% by weight of an essential oils blend, such as orange, grapefruit and peppermint oils to enhance the aroma given off by the basic composition.

The composition is applied as a lotion to the skin adjacent the hairline prior to dyeing the hair and when applied to the skin it forms a peel or skin like mask which will protect the skin from dye. The mask can be peeled off the skin once the hair has been dyed without hurting the person and while removing any dye thereon. The formula is enriched with essential oils, tightens the skin, is hypo-allergenic, acts as a skin moisturizer and is water soluble. It creates a protective film barrier which gently peels away removing any hair dye that may have gotten thereon.

The process of preventing coloring of the skin adjacent the hairline when dyeing a person's hair includes preparing the composition in a lotion for applying to a person's skin adjacent the hairline and then applying the composition as a lotion along the hairline of a person before dyeing their hair to form a peelable coating over the skin adjacent the hairline. The person's hair is then dyed and the mask is peeled from the person's skin after the hair has been dyed to remove the mask and any dye that may have gotten thereon.

EXAMPLE

|  |  |
|---|---|
| Alcohol SD-40A | 20% |
| Polyvinylpyrrolidone | 10% |
| Glycerin | 1% |
| Ethylhexyl Palmitate | 3.7% |
| Steareth-10 | 2.1% |
| *Bambusa vulgaris* Extract | 3% |
| Aluminum Starch Octenylsuccinate | 3% |
| Zinc Oxide | 1% |
| Titanium Dioxide | 1% |
| Dimethicone | 1.5% |
| Peg-400 polyethylene | 3% |
| Allantoin | 0.2% |
| Essential Oils Blend | 0.5% |
| Water | 50% |
| Total: | 100% |

It should be clear at this point that a method of dying a person's hair has been provided and especially a method and composition for preventing coloring of the skin adjacent the hairline when dying a person's hair. It should also be clear that the composition provides a simple peel-able mask which can be easy and quickly removed with inconvenience to a person having their hair dyed. However the present invention is not to be construed as limited to the example given which is to be considered illustrative rather than restrictive.

I claim:

1. A method of preventing coloring of the skin adjacent the hairline when dyeing a person's hair comprising the steps of:
preparing a composition consisting essentially of 2-20% by weight of alcohol, 1-8% by weight of polyvinylpyrrolidone, 1-10% by weight of polyvinyl alcohol, about 1% by weight of glycerin, 1-15% by weight of ethylhexyl palmitate, 0.5-5% by weight of bambusa vulgaris extract, 0.2-5% by weight of steareth, 0.5-5% by weight of aluminum starch octenylsuccinate, 0.5-5% by weight of zinc oxide, 0.5-5% by weight of titanium dioxide, 1-10% by weight of polyethylene glycol, 0.5-10% by weight of dimethicone, 0.05-1% by weight of allantoin and 30-70% by weight of water;
applying said composition along the hairline of a person before dyeing their hair to form a film mask over the skin adjacent the hairline;
dyeing said person's hair; and
peeling off the film mask from the person's skin after the hair has been dyed to thereby remove dye that may have gotten thereon.

2. The method of preventing coloring of the skin adjacent the hairline when dyeing a person's hair in accordance with claim 1 in which the composition includes about 3.7% by weight of ethylhexyl palmitate.

3. The method of preventing coloring of the skin adjacent the hairline when dyeing a person's hair in accordance with claim 2 in which the composition steareth includes about 2% by weight of steareth-10.

4. The method of preventing coloring of the skin adjacent the hairline when dyeing a person's hair in accordance with claim 3 in which the composition alcohol includes polyvinyl alcohol and alcohol SD-40A.

5. The method of preventing coloring of the skin adjacent the hairline when dyeing a person's hair in accordance with claim 4 in which the composition includes about 3% by weight of bambusa vulgaris extract.

6. The method of preventing coloring of the skin adjacent the hairline when dyeing a person's hair in accordance with claim 5 in which the composition includes about 3% by weight of aluminum starch octenylsuccinate.

7. The method of preventing coloring of the skin adjacent the hairline when dyeing a person's hair in accordance with claim 6 in which the composition glycerin includes glyceryl acrylate/acrylate acid copolymer.

8. The method of preventing coloring of the skin adjacent the hairline when dyeing a person's hair in accordance with claim 7 in which the composition includes about 3% by weight of polyethylene glycol.

9. The method of preventing coloring of the skin adjacent the hairline when dyeing a person's hair in accordance with claim 8 in which the composition contains about 1.5% by weight dimethicone.

10. The method of preventing coloring of the skin adjacent the hairline when dyeing a person's hair in accordance with claim 9 in which the composition contains about 1% by weight of zinc oxide.

11. The method of preventing coloring of the skin adjacent the hairline when dyeing a person's hair in accordance with claim 10 in which the composition contains about 1% by weight of titanium dioxide.

12. The method of preventing coloring of the skin adjacent the hairline when dyeing a person's hair in accordance with claim 11 in which the composition contains about 0.2% by weight of allantoin.

* * * * *